United States Patent [19]

Neuert et al.

[11] Patent Number: 5,214,828
[45] Date of Patent: Jun. 1, 1993

[54] PROCESS AND APPARATUS FOR GUIDING A TOW

[75] Inventors: Richard Neuert; Bernd Huber, both of Kelheim, Fed. Rep. of Germany

[73] Assignee: Hoechst, Fed. Rep. of Germany

[21] Appl. No.: 679,224

[22] Filed: Apr. 2, 1991

[30] Foreign Application Priority Data

Apr. 4, 1990 [DE] Fed. Rep. of Germany ...... 4010831

[51] Int. Cl.$^5$ .............................................. D01D 11/02
[52] U.S. Cl. ........................................ 28/282; 28/268; 28/248
[58] Field of Search ............... 28/282, 263, 265, 268, 28/269, 248

[56] References Cited

U.S. PATENT DOCUMENTS

| | | | |
|---|---|---|---|
| 2,914,810 | 12/1959 | Robinson et al. | 28/269 X |
| 3,017,684 | 1/1962 | Pittman | 28/248 |
| 3,358,436 | 12/1967 | Niina et al. | 28/282 X |
| 3,386,145 | 6/1968 | Harris | 28/282 X |
| 3,528,149 | 9/1970 | Tambini et al. | 28/269 X |
| 3,586,445 | 6/1971 | Martin | 28/282 X |
| 3,708,832 | 1/1973 | Lohrke | 28/282 X |
| 3,713,729 | 1/1973 | Inoue et al. | 28/282 X |
| 3,729,777 | 5/1973 | Hoffman et al. | 28/282 |
| 3,763,520 | 10/1973 | Izawa et al. | |
| 4,301,579 | 11/1981 | Van den Hoven. | |
| 4,369,555 | 1/1983 | Nikkel | 28/248 X |
| 4,519,116 | 5/1985 | Aberle et al. | 28/257 |
| 4,528,631 | 7/1985 | Bogucki-Land | 28/185 X |
| 4,573,856 | 3/1986 | Meyer et al. | 414/561 |
| 4,750,964 | 6/1988 | Hettinger, Jr. et al. | 28/185 X |
| 4,794,678 | 1/1989 | Reim et al. | 28/107 |
| 5,114,087 | 5/1992 | Fisher et al. | 28/194 X |

FOREIGN PATENT DOCUMENTS 962516 12/1962 United Kingdom .
2023675 1/1980 United Kingdom ................ 28/282

Primary Examiner—Clifford D. Crowder
Assistant Examiner—Bibhu Mohanty
Attorney, Agent, or Firm—Connolly & Hutz

[57] ABSTRACT

A process and apparatus for guiding a continuous moving tow in synthetic fiber manufacture. The profile (the thickness distribution and width) and the position of the tow are continuously sensed in a non-contact manner and an appropriate electrical signal is generated. This electrical signal is used to control the profile and the position of the tow in such a way that its profile and position stay within predetermined target value ranges. The tow geometry is preferably sensed using a CCD camera, while the tow geometry is controlled using tow-engaging deflecting means. In this way it is possible to optimize tow profile and position, for example for entry into a stuffer box (FIG. 1).

16 Claims, 3 Drawing Sheets

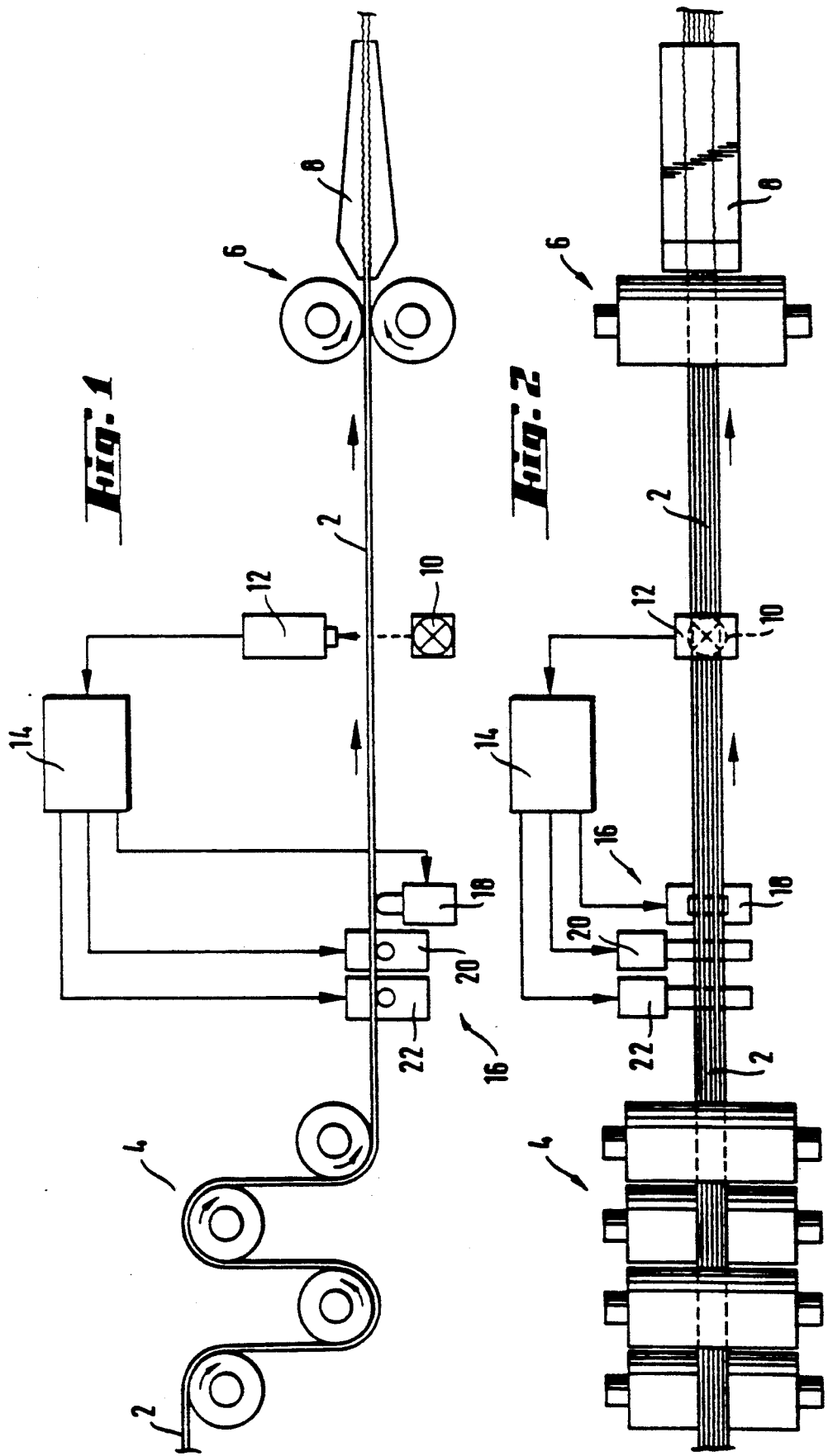

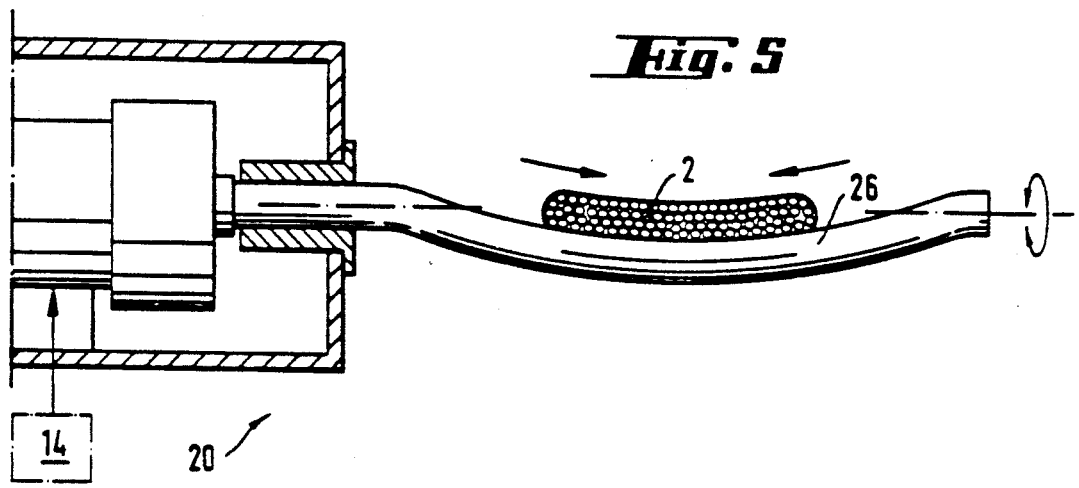
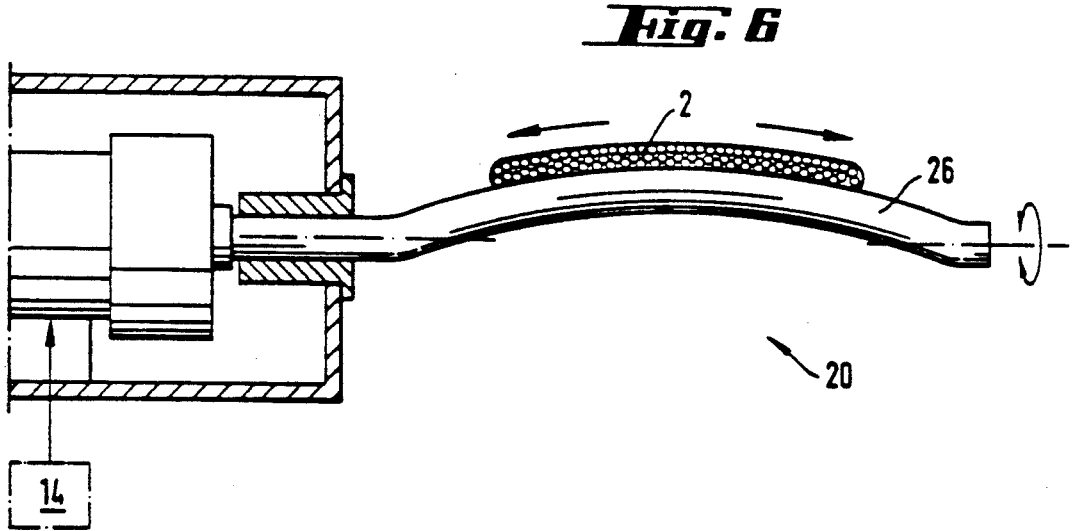
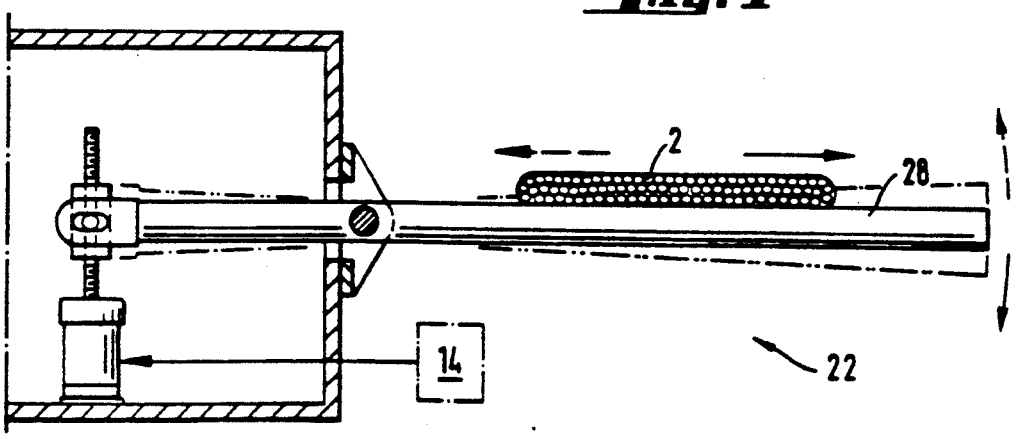

PROCESS AND APPARATUS FOR GUIDING A TOW

The invention relates to a process and apparatus for guiding a continuous moving tow in synthetic fiber manufacture. Such a tow comprises a bundle of a few thousand to several million filaments, in particular prior to entry into a stuffer box crimping machine.

It is known that the quality, in particular the uniformity, of crimped synthetic fiber tows or of staple fibers produced therefrom depends significantly on the uniformity of the feed tow. For this reason there have already been proposed devices which are supposed to produce a tow of uniform thickness, for example crowned rolls (DE 17 85 028), guides with grooves (U.S. Pat. No. 43 01 579), lateral guides (DE 14 35 438) or doubly frustoconical rollers (DE 16 60 291).

There have also been several proposals for processes in which the feed tow is composed of a multiplicity of subsidiary tows (GB 962 516, DE 21 44 763, EP 199,238). These processes are based on the principle that the faults of the subsidiary tows will on average be canceled out by the process of doubling.

DE 33 06 867 discloses a process and apparatus for guiding a continuous moving tow prior to entry into a stuffer box crimping machine wherein the tension of the tow is measured continuously and the speed of the feed rollers of the crimping machine is controlled as a function thereof. However, this does not make it possible to optimize the geometry of the tow.

It is an object of the invention to specify a process and apparatus for guiding a continuous moving tow in synthetic fiber manufacture which permit an optimization of the geometry of the tow.

To achieve this object the process of the present invention comprises the non-contact sensing of at least one geometric variable or of a property of the tow which is representative of this geometric variable and controlling the geometric variable of the tow in such a way that it stays within a predetermined target value range.

The non-contact sensing is advantageously effected electro-optically. This preferably means measuring the intensity of a light beam transmitted or reflected by the tow. This permits a statement about the tow profile (thickness and width of the tow) and the position of the tow in the transverse direction.

The characteristic variables which are sensed for the tow profile are preferably the thickness of the tow across its width and/or the width of the tow and/or the position of the tow in the transverse direction.

These geometric variables are then continuously controlled, preferably by deflecting means engaging with the tow, in such a way that they stay within predetermined target value ranges.

The sensing and controlling is advantageously carried out section by section in strip-shaped subsidiary regions distributed across the width of the tow.

In this way it is possible for example to maintain an optimal rectangular tow cross-section as well as an optimal position of the tow in the transverse direction (on the transport godet). This makes it possible to continuously present a tow of optimal geometry to the downstream crimping machine. Therefore, uniform crimping across the entire tow width is obtained. The crimping box width is utilized to a very high degree. Moreover, the textile further processibility of the tow fiber is improved.

It will be readily understood that the process of the present invention is usable not only prior to entry into a crimping machine but in general wherever optimal tow geometry is important, for example for entry into a dryer.

An apparatus for carrying out the process of the present invention comprises a non-contact sensor means (10; 12) which measures the geometric variable or the property of the tow (2) which is representative thereof and generates a corresponding electrical measurement signal, a signal processing means (14) which generates a control signal as a function of the measurement signal, and a control unit (16) which controls the geometric variable of the tow (2) as a function of the control signal.

Preferably, the sensor means comprises a light source (10) which illuminates the tow and an electronic camera (12) which detects the light transmitted or reflected by the tow (2). The camera can be a video camera, but preferably is a CCD line or matrix camera. The light source and the camera can be arranged on the same side of the tow. Preferably, the light source and the camera are arranged on opposite sides of the tow, since the transmitted light process permits a more accurate statement about the geometric variables of the tow to be monitored.

The control unit (16) preferably comprises one or more tow-engaging deflecting means (18; 20; 22) for controlling the thickness and/or width and/or position of the tow (2). A deflecting means for controlling the thickness of the tow comprises a series of at least two side-by-side deflecting elements (24) which are movable perpendicularly to the tow plane and transport direction and which are movable independently of each other in the direction of the tow (2) for the purpose of widening it out locally. To control the width and position of the tow preference is given to using straight or curved deflecting bars or rollers which extend transversely to the tow and are tiltable or rotatable about their longitudinal axis respectively.

The process of the present invention and an apparatus for carrying it out will be further described with reference to drawings, where FIG. 1 shows a diagrammatic side elevation of an apparatus for guiding a tow;

FIG. 2 shows a plan view of the apparatus of FIG. 1;

FIGS. 5 and 6 show a deflecting means for controlling the width of the tow in various operating states; and FIG. 7 shows a deflecting means for controlling the lateral position of the tow.

Figure 3:
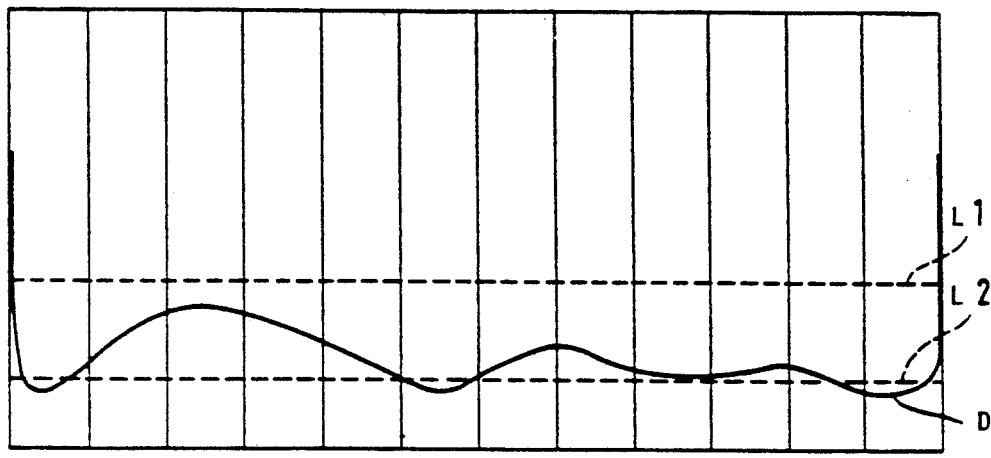
FIG. 3 shows a screen for visualizing a measurement signal corresponding to the tow profile.

The apparatus shown in FIGS. 1 and 2 for guiding a tow (2) comprises feed rollers (4) and take-off rollers (6) which in the depicted embodiment also form the intake rollers of a stuffer box (8). The tow (2) comprises a multiplicity of filaments and has for example the cross-section depicted in FIG. 4.

Underneath the running track for the tow (2) is a light source in the form of a lamp (10) which sends a light beam upward in the direction of the tow (2). On the light source (10) remote side of the tow (2) is a camera (12) which measures the intensity of the light transmitted by the tow (2). The camera (12) is for example, a CCD line camera (as marketed for example by Honeywell under the designation HVS 256). The line camera should have a resolution of at least 128 gray tone levels and in this specific illustrative embodiment detects 256 gray tone levels.

The measurement signal generated by the camera (12), which represents the intensity of the light transmitted by the tow (2) versus the width of the tow, passes to a signal processing means (14) in the form of an arithmetic processing unit which generates control signals for actuating a control unit (16).

The control unit (16) of the depicted embodiment comprises a deflecting means (18) for controlling the thickness of the tow (2), a deflecting means (20) for controlling the width of the tow (2) and a deflecting means (22) for controlling the position of the tow (2) in the transverse direction. The deflecting means (18, 20 and 22) are arranged in series in such a way that, viewed in the tow transport direction, first the lateral position, then the width and then the thickness of the tow (2) are controlled.

Figure 4:
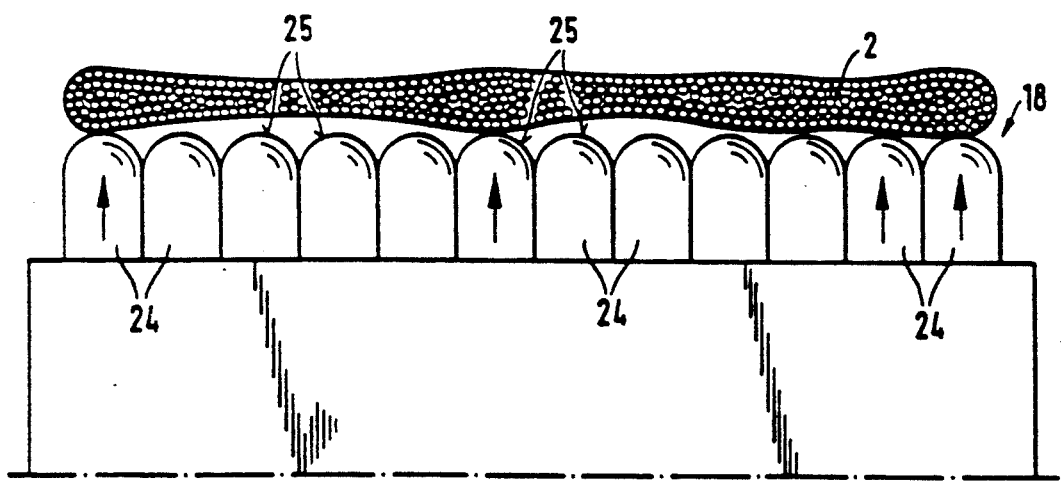
FIG. 4 shows a tow profile with a deflecting means for controlling the thickness of the tow.

As indicated diagrammatically in FIG. 4, the deflecting means (18) comprises a series of side-by-side deflecting elements (24) in the form of vertically disposed rods which are axially displaceable independently of each other. Each deflecting element (24) has a rounded-off end (25) which can penetrate into the tow (2) in order to locally widen out the tow (2) and thereby reduce its thickness.

As is diagrammatically indicated in FIGS. 5 and 6, the deflecting means (20) comprises a curved deflecting bar (26) which extends transversely to the longitudinal direction of the tow (2). The deflecting bar (26) is rotatable about its longitudinal axis, so that the tow (2) rests against the convex or concave side of the deflecting bar (26). If the tow (2) rests against the concave side of the deflecting bar (26) (FIG. 5), this results in a reduction of the width of the tow (2). If, by contrast, the deflecting bar (26) engages with the tow (2) with its convex side, this enlarges the width of the tow (2).

The deflecting means (22) shown in FIG. 7 for controlling the position of the tow (2) comprises a straight deflecting bar or roller (28) which extends transversely to the longitudinal direction of the tow (2). As shown diagrammatically in FIG. 7, the deflecting bar (28) is tiltable at its left-hand (in the Figure) end. A pivoting movement of the deflecting bar (28) by at least ±0.1° results in a lateral shift of the tow (2) toward the right-hand side or toward the left-hand side (in FIG. 7).

Now the working principle of the apparatus will be described. It will be assumed that the tow (2) has at a certain point in time the profile shown in FIG. 4.

The line camera (12) then generates as a function of the light transmitted by the tow (2) an analog measurement signal D which represents the thickness distribution of the tow (2) in the plane of measurement. This analog signal D is further processed in the arithmetic processing unit (14) and can then be depicted on the screen of the arithmetic processing unit (14), as is shown diagrammatically in FIG. 3. FIG. 3 also shows a target value range for the signal D with an upper limit L1 and a lower limit L2.

As is further shown in FIG. 3, the screen is divided into a grid having a number (n) of strip-shaped subsidiary regions, n being 12 in the depicted embodiment. Each strip-shaped region is associated with a deflecting element (24) of the deflecting means (18) (FIG. 4). If the signal D which represents the thickness distribution infringes the upper or lower limits L1 and L2 respectively in one or more of the grid-shaped subsidiary regions, then the arithmetic processing unit (14) issues appropriate control signals to the deflecting means (18) in order to shift the associated deflecting elements (24).

In the depicted embodiment, the signal D infringes the lower limit L2 in the first, sixth, eleventh and twelfth subsidiary region (viewed from the left). This means that the tow (2) is excessively thick in these subsidiary regions. Consequently, the first, sixth, eleventh and twelfth deflecting element (24) are moved into the tow (2) in order to widen out the tow in these subsidiary regions and thus reduce its thickness locally.

The comparison of signal D with the target value range defined by the limits L1 and L2 can additionally be represented using a diode strip (not shown). For example, each strip-shaped subsidiary region can be coordinated with two diodes, of which one lights up in the event of infringement of the upper limit while the other lights up in the event of infringement of lower limit and the two diodes do not indicate any signal when the signal D is within the target value range.

The signal D is also used for determining the actual width and actual position of the tow 2. In the event of limit value infringements the arithmetic processing unit (14) issues appropriate control signals to the deflecting means (20) and (22) for correcting the width and position of the tow.

In this way the tow profile (thickness and width) and the position of the tow are continuously maintained within optimal ranges in an on-line process.

If limit value infringements occur in the evaluation of signal D by the arithmetic processing unit (14), the output is an error log showing the time and the type of error. The CCD line camera should for example make a recording at a time interval of at least 5 ms.

Instead of a CCD line camera it is of course also possible to use a CCD matrix camera. In this case the result will be not an individual measurement line but a matrix-shaped measurement field which requires appropriate signal evaluation in the arithmetic processing unit. However, the method for controlling the tow geometry is the same as with the use of a line camera.

What is claimed is:

1. A process for guiding a continuous moving tow in synthetic fiber manufacture in which a property of the tow is continuously monitored and controlled as a functioning of this monitoring, which comprises the non-contact sensing of at least one geometric variable or of a property of the tow which is representative of this geometric variable and controlling the thickness of the tow across its width by tow engaging means in such a way that it stays within a predetermined target value range.

2. The process of claim 1, wherein the sensing is effected electro-optically.

3. The process of claim 1, wherein the intensity of a light beam reflected by the tow is sensed.

4. The process of claim 1, wherein the thickness of the tow across its width is sensed.

5. The process of claim 1, wherein the sensing and controlling is carried out section by section in strip-shaped subsidiary regions distributed across the width of the tow.

6. Apparatus for guiding a continuous tow comprising a non-contact sensor means which measures a geometric variable or a property of the tow which is representative thereof and generates a corresponding electrical measurement signal, signal processing means which generates a control signal as a function of the measurement signal, and a control unit comprising at least one tow engaging deflecting means for controlling the thickness of the tow as a function of the control signal.

7. Apparatus of claim 6, wherein the sensor means comprises a light source which illuminates the tow and an electronic camera which detects the light transmitted or reflected by the tow.

8. Apparatus of claim 7, wherein the light source and the camera are arranged on opposite sides of the tow.

9. Apparatus of claim 7, wherein the camera is a CCD line or matrix camera.

10. Apparatus of claim 7, wherein the camera is capable of detecting at least 128 gray tone levels.

11. Apparatus of claim 6, wherein the deflecting means for controlling the thickness of the tow comprises a series of at least two side-by-side deflecting elements which are movable perpendicularly to the tow plane and transport direction and which are movable independently of each other in the direction of the tow for the purpose of widening it out locally.

12. Apparatus of claim 11, wherein the deflecting elements comprise axially displaceable rods which engage with the tow with rounded-off ends.

13. Apparatus of claim 6, wherein the deflecting means for controlling the width of the tow comprises at least one curved deflecting bar whose longitudinal axis extends perpendicularly to the tow transport direction and essentially parallel to the tow plane and which is rotatable about its longitudinal axis.

14. Apparatus of claim 6, wherein the deflecting means for controlling the position of the tow in the transverse direction comprises at least one straight deflecting bar or roller whose longitudinal axis extends perpendicularly to the tow transport direction and parallel to the tow plane and which is tiltable about an axis which extends parallel to the tow transport direction.

15. Apparatus of claim 8, wherein the camera is a CCD line or matrix camera.

16. Apparatus of claim 8, wherein the camera is capable of detecting at least 128 gray tone levels.

* * * * *